United States Patent [19]

Burton et al.

[11] Patent Number: 5,175,190
[45] Date of Patent: Dec. 29, 1992

[54] MEDIUM CHAIN FATTY ACIDS OF C8-10 FOR THE TREATMENT OF SKIN LESIONS

[75] Inventors: Albert F. Burton; David McLean, both of Vancouver, Canada

[73] Assignee: The University of British Columbia, Vancouver, Canada

[21] Appl. No.: 656,404

[22] Filed: Feb. 15, 1991

[51] Int. Cl.⁵ .............................................. A61K 31/20
[52] U.S. Cl. .................................. 514/560; 514/859; 514/863
[58] Field of Search ......................................... 514/560

[56] References Cited

U.S. PATENT DOCUMENTS

| | | | |
|---|---|---|---|
| 4,343,798 | 9/1982 | Fauzi | 514/179 |
| 4,346,109 | 8/1982 | Yamatsu et al. | 514/560 |
| 4,507,319 | 3/1985 | Barratt et al. | |
| 4,612,331 | 9/1986 | Barratt et al. | |

FOREIGN PATENT DOCUMENTS 232982 8/1987 European Pat. Off. .

OTHER PUBLICATIONS

R. W. Turnell and A. F. Burton, "Glucorticoid Receptors and lymphocytolysis in normal and neoplastic lymphocytes", Molecular & Cellular Biochemistry, 9, 175–189 (1975).
A. F. Burton and L. H. Piette, "Spin labelling studies of cytolysis induced by fatty acids", Molecular & Cellular Biochemistry, 51, 73–78 (1983).
A. F. Burton and W. L. Dunn, "Role of anions in the lymphocytolytic action of corticosteroids and fatty acids", Molecular & Cellular Biochemistry 63, 125–129 (1984).
A. F. Burton, J. M. Storr and W. L. Dunn, "Cytolytic action of corticosteroids on thymus and lymphoma cells in vitro", Canadian Journal of Biochemistry 45, 289–297 (1967).
Chemical Abstracts 98: 113737n (1983).
Francoeur et al —Pharmaceutical Research, vol. 7, No. 6 (1990).

*Primary Examiner*—Leonard Schenkman
*Attorney, Agent, or Firm*—Barrigar & Oyen

[57] ABSTRACT

This invention pertains to the use of medium chain fatty acids (C8-10) in the treatment of skin lesions. More particularly, the invention relates to a preparation containing medium chain fatty acids (C8-10) which has beneficial effects when applied topically in skin conditions, including acne, psoriasis, chronic conditions considered to be pre-cancerous lesions, and malignant lesions of skin. A composition for topically treating skin lesions which comprises a fatty acid of a carbon number from 8 to 10 having a free carboxyl group and a pharmaceutically acceptable carrier.

6 Claims, No Drawings

MEDIUM CHAIN FATTY ACIDS OF C8-10 FOR THE TREATMENT OF SKIN LESIONS

FIELD OF THE INVENTION

This invention pertains to the use of medium chain fatty acids (C8-10) in the treatment of skin lesions. More particularly, the invention relates to a preparation containing medium chain fatty acids (C8-10) which has beneficial effects when applied topically in skin conditions, including acne, psoriasis, chronic conditions considered to be pre-cancerous lesions, and malignant lesions of skin.

BACKGROUND OF THE INVENTION

Substantial experimental work has been conducted for a number of years on the effects of fatty acids on various rat and mouse tumours. This work includes observed damage and obliteration of tumours in treated animals without apparent toxicity. (See Burton A. F., et al., Molecular & Cellular Biochemistry publications: 1975:9:175; 1983:51:73; 1984:63:125; and Can. Journal of Biochemistry 1967:45:289.)

Several patents disclose the use of fatty acid-related compounds in the treatment of skin disorders. European Patent No. 232982, Aug. 19, 1987, discloses the use as a curative agent of 2-hydroxyoctanoic acid (I), 2-ketooctanoic acid (II) and their 2-6C alkyl esters and di- and tri-glyceride esters in the preparation of pharmaceutical compositions for treating certain skin disorders. The compositions are purportedly useful for treating, among other things, ichthyosiform dermatoses, especially ichthyosis vulgaris, sex-linked ichthyosis, lamellar ichthyosis and epidermolytic ichthyosis.

U.S. Pat. No. 4,507,319, Mar. 26, 1985, discloses the treatment of skin disorders by the application of a composition containing 0.1-20% by weight 2-hydroxyoctanoic acid, 2-ketooctanoic acid or their mixtures and a neutralising agent to adjust the pH to 3-7. The neutralising agent has a cation whose ionic radius is at least 100 pm ($10^{-12}$m). Suitable neutralising agents include KOH, NH4OH or amines, especially mono-, di- or tri-alkanolamines. The composition may also contain alkyl lactates, (3-6C) 2-hydroxyalkanoic acids, (3-6C) ketoalkanoic acids and a (1-4C) alkanol. A humectant such as a (2-4C) alkanediol or its dimer or trimer may also be present as well as other skin treating agents such as zinc sulphate, beta-cyclodextrin, sodium desoxycholate, allantoin (anti-inflammatory), salicylic acid or tetracycline (antibacterial).

U.S. Pat. No. 4,612,331 discloses a cosmetic aqueous composition for topical applications to human skin, comprising (a) 0.1-20 wt. % of 2-hydroxyoctanoic acid; (b) 0.1-20 wt. % of hydroxypropionic acid; and (c) alkanolamine in sufficient amount to adjust pH to 3.8-4.5.

Japanese Patent No. 58170713, Oct. 7, 1983, discloses a composition for application to skin for stain, lentigo, and papilla. The composition contains as active ingredient, 0.1 to 40 wt. % of dicarboxylic acid having 7 to 13 carbon atoms of formula of (wherein n is 5 to 11, R1 is glyceryl, R2 is glyceryl or H, that is diglyceryl and a combination of glyceryl and H). The composition is useful for curing or improving stain, lentigo and papilla by application to skin. The dicarboxylic acid compound includes mono- or di-glyceryl pimelate, mono- or di-glyceryl suberate, mono- or di-glyceryl 1,9-nonamethylene dicarboxylate, mono- or di-glyceryl 1, 10-decamethylene dicarboxylate, mono- or di-glyceryl 1, 11-undecamethylene dicarboxylate etc.

SUMMARY OF THE INVENTION

The invention is directed to composition for topically treating skin lesions which comprises a fatty acid of a carbon number from 8 to 10 having a free carboxyl group and a pharmaceutically acceptable carrier. The fatty acid can be a C8-10 acid and the carrier can be a substance which promotes the absorption of the fatty acid into the skin.

The composition may include geranic acid and oleic acid. The geranic acid may comprise about 5 to about 35 percent of the composition.

The invention is also directed to a method of treating skin lesions which comprises applying topically to the surface of the lesion a composition comprising a fatty acid having a carbon number from 8 to 10 having a free carboxyl group and a pharmaceutially acceptable carrier. The skin lesion may be acne, psoriasis or a pre-cancerous condition.

The invention is also directed to a composition for treating skin lesions comprising:

| | |
|---|---|
| 3,7-dimethyl, 6,7-dihydroxyoct-2-enoic acid (MHA) | 15 g |
| Oleic acid | 7.5 g |
| Stearyl alcohol | 10 g |
| Sodium dodecyl sulfate (SDS) | 1.3 g |
| Oil of gardenia | 1 g |
| Water | 65 ml |

The invention is also directed to a method of preparing a composition for treating skin lesions comprising:

(a) heating MHA, oleic acid and stearyl alcohol to 60° C. to melt them together, and then mixing with water containing the dissolved SDS and heating to 60° C., the mixture being emulsified by mixing at high speed, the gardenia oil being added during the mixing.

(b) refrigerating the preparation and letting stand for two days to allow escape of air. The preparation is subsequently kept refrigerated. This formulation might be stabilized by the addition of other agents, but it is stable and of suitable consistency when kept refrigerated.

DETAILED DESCRIPTION OF THE INVENTION

The novel use for medium chain fatty acids in a composition for the treatment of skin lesions of various types, including acne, psoriasis and pre-cancerous lesions and cancers such as melanomas, is based upon observations made on the effects of various fatty acids on tumour and other cells. Some cells have the capacity to absorb large amounts of fatty acids without damage, whereas other cells are destroyed by the fatty acids. For example, fatty acids, at about 1% of the amount which liver cells can absorb, will destroy all tumour cell types examined as well as lymphocytes and other cells. The fatty acids cause changes in the membranes of these cells which lead, eventually, to cytolysis, or death of the cell.

The manner in which fatty acids damage tumour cells differs from that of all other known anti-tumour agents. The effects of fatty acids are not based upon effects upon cells which are growing, as are other agents, and therefore the effects of fatty acids would probably potentiate the action of other agents.

Medium chain triglycerides are so called because the three fatty acids which are combined with glycerol are of a molecular size intermediate between short chain and long chain fatty acids. Short chain fatty acids have up to four carbon atoms in the molecule; medium chain fatty acids have C5–C10; long chain fatty acids have C12 or more. Fatty acids which are C12 are intermediate in behaviour between the medium and the long chain fatty acids.

Medium chain fatty acids, having a carbon number from C5 to C10, such as caprylic (octanoic) acid, cannot be utilized by cells for anything but as a source of energy. They are not stored. Medium chain fatty acids C8 or higher can exert the same anti-tumour action as other fatty acids, but ultimately, are oxidized as is any other fat.

Medium chain fatty acids penetrate skin about 100 times faster than longer chain fatty acids, and accumulate to a high concentration in an area where applied, to destroy susceptible cells and then ultimately be disposed of by the cell, being used as a fuel similar to native fats.

Short chain fatty acids are common intermediates formed during metabolism of various substances including carbohydrates and protein. All the fatty acids in animal bodies which serve either as structural components or as fuel storage are long chain fatty acids of C16 or more. The medium chain fatty acids are relatively uncommon, but a prominent source is coconut and palm oil where C12 fatty acids makes up almost half; about 20% is medium chain fatty acids.

Medium chain fatty acids have properties which differ from the usual dietary fats and which can be of advantage in certain circumstances. This includes the manner in which they are absorbed from the digestive tract and the manner in which they are used by tissues.

Normal fat is partly broken down in the intestine to its constituent fatty acids and monoacyl glycerol (glycerol with one fatty acid) which then pass through the cell walls and enter the intestinal cells. Here they are reassembled to triglyceride. These fats, including other fatty substances, fat-soluble vitamins, cholesterol, etc., are formed into microscopic droplets about 1 micron ($10^{-6}$ metre) diameter with detergent-like constituents forming a coat about the surface. These substances, phospholipids—mostly lecithin—are molecules with a water-soluble part and a fat-soluble part on the same molecule—a "surfactant". The particles, chylomicra, are thus stable in blood, with the fatty interior shielded from water, and this allows transport of fatty substances in the blood without coalescence of droplets. The milky chylomicra are secreted from the gut into lymphatic channels which ultimately empty into the bloodstream where they will circulate for 1–2 hours after a meal before being cleared by the adipose tissue storage depots, mainly.

Unlike most fats, medium chain triglycerides are rapidly split in the digestive tract to three fatty acids and glycerol which are absorbed directly into the bloodstream without being formed into chylomicra. In the blood, they are bound to the protein, albumin. They enter the liver via the portal vein and most are broken down to ketone bodies, water-soluble derivatives whose only fate is to be oxidized by tissues for energy. The medium chain fatty acid which passes the liver circulates for several hours, being taken up directly by tissues. Here, another difference from normal fatty acids is evident. Normal fatty acids require a factor, carnitine, which must interact with the fatty acid to permit its entry into the site in the cell where enzymes will oxidize it. Medium chain fatty acids, however, do not require this "carnitine shuttle" and enter directly into the tissues in a rapid manner. Accordingly, medium chain fatty acids are oxidized about ten times faster than other fatty acids by the tissues. Very little conversion to other substances occurs, most medium chain fatty acids are oxidized in preference to any other fuel available to the tissues.

Fatty acids of C8 or higher can cause lysis of cells, including tumor cells if they accumulate to an amount which exceeds the capacity of the cells to dispose of them. This property of fatty acids can be exploited in certain circumstances to effect the destruction of tumor cells. The ingestion of moderate, nutritional quantities of medium chain triacylglycerides results in an influx of the fatty acids into the liver via the portal system at a rate which, while easily handled by the liver and beyond that, the lung, can cause lysis of tumor cells in those tissues. Since these two organs are major sites for the development of primary, and especially of secondary tumor masses, this property could be beneficial and is without toxicity. Some fatty acids, by virtue of their structure, can themselves resist oxidation, and can block the oxidation of other fatty acids in tissues. These could be used alone or included to potentiate the lytic action of other fatty acids. The direct local application of fatty acid preparations on tumors can also be used to obtain reduction of tumor mass, either alone or as an adjunct to other forms of therapy. Such applications can be especially useful in the treatment of skin lesions and even internal growths which are not resectable and do not respond to existing modes of therapy.

The cytolytic effect of free fatty acids has been shown to depend upon uptake by cells of an amount in excess of their capacity for metabolizing it. The excess free fatty acids insert into the nuclear membrane increasing its fluidity. This is followed by an influx of chloride ion and nuclear edema, which progresses with time to karyorrhexis and cell lysis. Many cells examined, including all of a variety of rodent tumor cells, cannot survive uptake of 1 $\mu$mol/g tissue without lysis. Liver, adipose tissue, lung and intestinal mucosa can withstand up to several orders of magnitude greater quantities of free fatty acids, having proteins which bind, or enzymes which metabolize them. The process of lysis requires several hours, but uptake is rapid and irreversible damage can be maximal by two min.

There is no regulation to uptake of free fatty acids by cells. Regulation is all over the release of free fatty acids which are transported bound to serum albumin, with a $T_{\frac{1}{2}}=2$ min. The albumin is rarely saturated to more than a fraction of its capacity.

Absorption of chemotherapeutic agents through skin for treatment of other than skin disorders is a relatively recent development. The major barrier is the stratum corneum and it is believed that the permeability is determined by extracellular lipids. This barrier is greatly reduced by oleic acid, which enhances absorption. Absorption of lipophilic agents in quantities of mg/cm$^2$/day with penetration into deeper layers, for example, muscle and knee joint, is possible.

Recurrent local breast cancer involves skin lesions which are difficult to treat and are often unresponsive to current therapies. It seems feasible that percutaneous absorption of free fatty acids is a novel mode of treatment without systemic effects. The mechanism of action of free fatty acids is completely different from nearly all existing oncolytic drugs and is not related to rate of growth or cell cycle. It might be adequate by itself, but would synergize other agents for this reason.

Caprylic acid (C8:0), octanoic acid) is lytic and has almost no other fate than to be oxidized in the body in preference of other substrates. It is absorbed through the skin 100 times faster than oleic acid (C18:1$^{\Delta 9}$). However, oleic acid enhances the uptake of other lipophilic compounds by twentyfold.

Geranic acid is a derivative of octanoic, it is 3,5-dimethyl, 2,6-octadienoic acid, that is, has two methyl substituents and two trans double bonds. It can be derived from geranyl pyrophosphate on the cholesterol biosynthetic pathway, but mostly arises from oxidation of ingested precursors which are major constituents of the essence or aroma of fruits, for example, esters such as geranyl acetate, etc. The corresponding aldehyde, citral, has the characteristic scent of lemon. In liver and other tissues, these are converted to geranic acid. Geranic acid, by virtue of the C-3 methyl substituent, blocks $\beta$-oxidation of fatty acids. It can be oxidized readily in liver by an alternate route. (Refsum's disease, a rare genetic disorder, occurs when this pathway is deficient and these plant products accumulate). Geranic acid itself is lytic but also enhances the cytolytic effect of other fatty acids, by inhibiting their oxidation, increasing their toxic effect on tumor cells. Since caprylic acid has no other fate but oxidation, especially in tumor cells, the combination of the two locally can be strongly lytic to tumor cells under the area of application. Combined with oleic acid to enhance penetration, the three could provide a non-toxic mode of therapy which could nevertheless be effective locally in destroying tumor cells in skin.

Caprylic acid has a characteristic and unpleasant rancid odor, which is persistent. In order to combine desirable properties in an effective agent, derivatives of geranic acid were prepared, the most satisfactory derivative being 3,7-dimethyl, 6,7-dihydroxyoct-2-enoic acid (MHA) which has only a slight odor which is not objectionable. This is the medium chain fatty acid of choice. The preparation of MHA results in some residual geranic acid which does not affect the odor and is equally effective; its removal is difficult and unnecessary and geranic acid can be considered as an ingredient of minor content.

EXAMPLE 1

The process whereby fatty acids cause lysis of cells begins with insertion of fatty acids in the nuclear membrane causing a perturbance near the carboxyl end of the molecule and causing increased fluidity of the nuclear membrane. This is demonstrable by electron spin resonance and is maximal by 2 min. There follows an influx of chloride ion which leads to nuclear edema which is demonstrable by electron microscopy by 30 min. Over the next few hours, the disruption of chromatin and of nuclear processes leads to rupture of the nuclear membrane at several points, resulting in karyorrhexis and this ends in cytolysis. Those fatty acids of chain length C-8 or higher, whether unsaturated or substituted, are all effective in causing lysis, provided the carboxyl group is free.

We have established that the uptake of fatty acids by cells is dependent upon the concentration both of fatty acids and of albumin to which it binds in serum, and which regulates the uptake. A variety of rodent tumor cells and normal lymphocytes were found to behave in a similar manner: the uptake of fatty acids was essentially the same for all, depending on the concentration of fatty acids and albumin. There appeared to be no restriction of uptake and it continued as the concentration increased. Above a value of 0.6 $\mu$moles per gram of tissue, the capacity of the cells to metabolize the fatty acids was exceeded and damage began to occur, leading to lysis, a process which appears to be irreversible.

EXAMPLE 2

There are several tissues which, by virtue of efficient enzymatic mechanisms and of intracellular proteins which bind fatty acids as does albumin, have a very great capacity to handle high concentrations of fatty acids which they do in normal circumstances. These are liver, adipose tissue, intestinal mucosa and lung. The normal concentration of fatty acids entering these tissues at times is estimated to be much greater than most other cells, including tumor cells, can withstand. Accordingly, investigations were undertaken to explore the possibility that tumor cells growing in liver or lung, whether as primary or secondary growths, would take up such large quantities of fatty acids as the surrounding tissue, and if so, if this would cause lysis.

Rats used were of the Sprague-Dawley, Buffalo and NB strains, the latter two inbred, and tumors including the Walker 256 in rats, Morris hepatoma of Buffalo rats, NB$_2$ lymphoma of NB rats. Mice were of CD1 strain and hybrids B6D2F1/J which are a cross of (DBA/2×C57Bl/6J), carrying the transplanted tumor M114 which originated in the DBA/2 strain. Tumors were implanted in the liver by trocar and experiments carried out five or more days later when the tumors were established and were several mm in diameter. The uptake of fatty acids by liver and tumor tissues was followed using 1-$^{14}$C-oleic acid and 1-$^{14}$C-octanoic (caprylic) acid. These were diluted with unlabelled acid to determine the distribution of normal substrate levels of each fatty acid. Two preparations were tested: the sodium salt or soap of each was prepared, and an emulsion of each with 2.5% glycerol and 1.25% lecithin was prepared, giving stable droplets of $\leq 10$ $\mu$.

The uptake of 1-$^{14}$C-oleic acid by liver is shown for rats and mice in Table 1 including that of the Walker 256 tumor of rats.

TABLE 1

| | | | Uptake of 1-$^{14}$C-oleic acid | | | |
|---|---|---|---|---|---|---|
| Species | Tissue | Dosage | Preparation Administered | Time min. after inj. | Uptake, $\mu$/g tissue | No. animals |
| Rat | Liver | 20 $\mu$moles | salt, intraportal | 2 | 0.29 | (5) |
| Rat | Tumor (W256) | 20 $\mu$moles | salt, intraportal | 2 | 0.30 | (5) |
| Mouse | Liver | 50 $\mu$moles | salt, intraperitoneal | 30 | 2.48 | (21) |
| Mouse | Liver | 100 $\mu$moles | salt, intraperitoneal | 30 | 3.05 | (9) |
| Mouse | Liver | 100 $\mu$moles | emulsion, intraperitoneal | 30 | 2.30 | (5) |
| Mouse | Lung | 100 $\mu$moles | salt, intraperitoneal | 30 | 0.46 | (4) |

TABLE 1-continued

Uptake of 1-$^{14}$C-oleic acid

| Species | Tissue | Dosage | Preparation Administered | Time min. after inj. | Uptake. $\mu$/g tissue | No. animals |
|---------|--------|--------|--------------------------|---------------------|---------------------|-------------|
| Mouse | Liver | 100 $\mu$moles | emulsion. intraperitoneal | 30 | 1.68 | (5) |

Although the rat experiments did not result in a high uptake, it appeared that uptake by the tumor was the same as surrounding liver tissue. These tumors averaged 0.5 g, so were well developed when tested, with their own vascular system. Mice were injected with the fatty acids as a 1N solution which was mixed with 5% sucrose immediately before use. Each mouse was given 0.4 ml intraperitoneally which was found to give the optimum uptake by liver, which was maximal by 30 min.

The distribution of radioactivity was examined. Liver tissue was extracted with methanol: chloroform (1:2) and the chloroform phase was evaporated and spotted on thin layer chromatogram sheets. Autoradiograms were prepared and three zones were eluted, corresponding to esterified nonpolar lipids, fatty acids and phospholipids (Table 2).

TABLE 2

| Distribution of 1-$^{14}$C-oleic Acid in Liver Lipids | |
|---|---|
| Total Uptake: | 2.48 ± 0.33 $\mu$moles/g liver (21) |
| | % Distribution |
| Neutral nonpolar lipids: | 57.2 ± 4 |
| Phospholipids: | 30.8 ± 3 |
| Total esterified fatty acids: | 88.0 |
| Free fatty acids: | 12 |

Clearly, the fatty acids had been taken up and processed intracellularly.

In a few experiments, other tissues were examined. In one experiment in the rat, uptake by lung was the same as liver. Adipose tissue in mice varied and was sometimes much higher than liver after 30 min. In mice, portal blood after 30 min. contained 0.33 $\mu$moles/ml.

At this point, it was reasoned that caprylic (octanoic) acid, C8:0, might have advantages over oleic acid in reaching a higher concentration, even if for a brief period of time. From earlier experiments, it had been concluded that cells need only be exposed to a high concentration of fatty acids briefly and uptake will be high, and having taken it up, the cells must metabolize it or suffer damage. Caprylic acid is known to be rapidly absorbed from the gut directly into the bloodstream. It is not secreted from the gut as chylomicra, as is normal fat. Instead it enters the liver, bound loosely to albumin, via the portal vein. Caprylic acid is oxidized very rapidly by $\beta$-oxidation and mostly converted to ketone bodies. Very little is stored and that is first elongated and stored as palmitic acid. Considerably more caprylic than oleic is oxidized to $CO_2$.

Determining the uptake of 1-$^{14}$C-caprylic acid, as a salt and as an emulsion, presents problems of intepretation. Nevertheless, since ketone bodies which would be formed are water-soluble, the amount of radioactivity in esterified fat would give some indication of the amount entering the tissue, albeit an underestimate. This is shown in Table 3. All mice received 100 $\mu$moles intraperitoneally.

TABLE 3

Uptake of 1-$^{14}$C-caprylic acid by mouse tissues

| Tissue | Preparation | Time after injection | Uptake $\mu$moles/g tissue | No. mice |
|--------|-------------|---------------------|---------------------------|----------|
| Liver | salt | 10 | 2.75 | (5) |
| Liver | salt | 30 | 5.9 | (5) |
| Liver | emulsion | 10 | 1.97 | (5) |
| Liver | emulsion | 30 | 1.7 | (4) |
| Lung | salt | 10 | 0.60 | (4) |
| Lung | emulsion | 10 | 0.81 | (5) |
| Lung | emulsion | 30 | 2.21 | (4) |
| Tumor (intra-hepatic) | salt | 10 | 3.70 | (3) |

Clearly, the uptake of caprylic acid is high; considering the large amount known to be converted to water-soluble products, the initial uptake must have been considerably higher than that of oleic acid, as expected. In the tumor cells implanted in liver, around 80 mg in size, the uptake was clearly sufficient, according to all earlier observations, to bring about lysis.

Mice were implanted with tumors and the tumors allowed to grow for six days. At this time, the tumor is about 5 mm or so in diameter, weighing 30 mg, and its own vascularization is well established. Mice were injected once daily intraperitoneally with 100 $\mu$moles sodium caprylate, mixed with sucrose. Treatment continued for four days, then stopped. At day 20, the tumors had recurred, but were smaller, being about one week behind controls in growth. Tumors were treated and then removed a few hours later in order to examine the effects microscopically. After four hours, many cells with damaged nuclei were evident, similar to the cytological effects observed in vitro after treatment with fatty acids. After two injections, four hours apart, the tumor three hours later showed extensive destruction, with considerable lysis having occurred. In one instance where tumor cells had invaded the lung, these cells showed the same evidence of damage as in the liver.

When treatment was begun on day 4 following implantation at which time tumors are about 3 mm in diameter, the treated tumors were eradicated by day 8, the controls were about 5-6 mm diameter.

Rats implanted with the $Nb_2$ tumor did not tolerate ip injection of sodium caprylate well, as did mice. A few were given free caprylic acid orally and tumors examined four hours later. Treated tumors showed changes similar to those observed in mice.

It might be noted that when the triacylglyceride of caprylic acid, tricaprylin, was mixed with other ingredients into a cake and fed to mice for three days, with caloric intake normal for mice, the average consumption of caprylic acid per day was fifty times the quantity injected in the above experiments.

EXAMPLE 3

Treatment of a rat hepatoma in the inbred Nb strain of rats was conducted by implanting pieces of tumour tissue under the skin. After a month, these had grown to 5 to 10 mm in size. Application of a caprylic ointment to the overlying skin once daily for two days resulted in considerable shrinkage which was due to extensive necrosis of the tumours, reducing the size by about half. These experiments were designed to provide material for microscopic examination of the process under way.

EXAMPLE 4

A patient with malignant melanoma with multiple metastases volunteered to test this ointment. His condition was terminal but before his death, he reported that the skin metastases which were treated shrank visibly and flattened out in a day or two.

EXAMPLE 5

A patient with acneform lesions of long standing was treated daily with a caprylic ointment. The lesions cleared in a few days, remaining clear for several weeks.

In view of the demonstrated action of medium chain fatty acids on various cells, especially malignant cells, their use in treatment of skin cancer and of the very common pre-cancerous lesions of skin appears feasible.

FORMULATION

The preparation being tested consists preferably of 3,7-dimethyl, 6,7-dihydroxyoct-2-enoic (MHA) acid as the main ingredient plus oleic acid to facilitate absorption and stearyl alcohol to form a cream of suitable consistency. These ingredients were added to water containing sodium dodecyl sulfate as an emulsifying and antiseptic agent. Mixing was accomplished by use of a high speed stirring device with a sonicator, i.e. sound waves of high frequency. The fatty constituents are formed into stable microscopic droplets (10 micra or less). To this was added oil of gardenia to impart a pleasant odor.

| | |
|---|---|
| 3,7-dimethyl, 6,7-dihydroxyoct-2-enoic acid (MHA) | 15 g |
| Oleic acid | 7.5 g |
| Stearyl alcohol | 10 g |
| Sodium dodecyl sulfate (SDS) | 1.3 g |
| Oil of gardenia | 1 g |
| Water | 65 ml |

Possible variations might include fatty acids of chain length C-9 and C-10 which might be suitable and economical, derivatives of which might be used in a similar manner.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A method of treating acne, psoriasis, chronic pre-cancerous skin lesions and malignant skin lesions which comprises applying topically to the surface of the lesion a composition comprising a fatty acid having a free carboxyl group selected from the group consisting of 1-caprylic acid, 1-oleic acid, 3,5-dimethyl-2,6-octadienoic acid, and 3,7-dimethyl-6,7-dihydroxyoct-2-enoic acid, and pharmaceutically acceptable salts thereof, and a pharmaceutically acceptable carrier, wherein the fatty acid comprises about 5 to about 35 percent by weight of the composition.

2. A method as claimed in claim 1 wherein the skin lesion is acne, psoriasis or pre-cancerous.

3. A method according to claim 1, wherein the fatty acid is 3,7-dimethyl-6, 7-dihydroxyoct-2-enoic acid (MHA).

4. A method according to claim 1, wherein the fatty acid is 1-caprylic acid.

5. A method according to claim 1, wherein the fatty acid is 3,5-dimethyl-2, 6-octadienoic acid.

6. A method according to claim 1 wherein the fatty acid is 1-oleic acid.

* * * * *